United States Patent
Young

(10) Patent No.: US 6,626,906 B1
(45) Date of Patent: Sep. 30, 2003

(54) MULTI-PLANAR ADJUSTABLE CONNECTOR

(75) Inventor: Stuart Young, Memphis, TN (US)

(73) Assignee: SDGI Holdings, Inc., Wilmington, DE (US)

(*) Notice: Subject to any disclaimer, the term of this patent is extended or adjusted under 35 U.S.C. 154(b) by 188 days.

(21) Appl. No.: 09/694,228

(22) Filed: Oct. 23, 2000

(51) Int. Cl.$^7$ ............................................. A61B 17/56
(52) U.S. Cl. ........................................... 606/61; 606/73
(58) Field of Search ............................... 606/61, 73, 59, 606/60, 72

(56) References Cited

U.S. PATENT DOCUMENTS

| | | | | |
|---|---|---|---|---|
| 5,002,542 A | 3/1991 | Frigg | ........................... | 606/61 |
| 5,047,029 A | * 9/1991 | Aebi et al. | ..................... | 606/59 |
| 5,352,226 A | 10/1994 | Lin | .............................. | 606/61 |
| 5,486,174 A | 1/1996 | Fournet-Fayard et al. | .... | 606/61 |
| 5,575,791 A | 11/1996 | Lin | .............................. | 606/61 |
| 5,613,968 A | 3/1997 | Lin | .............................. | 606/61 |
| 5,785,711 A | 7/1998 | Errico et al. | .................. | 606/61 |
| 5,810,819 A | 9/1998 | Errico et al. | .................. | 606/61 |
| 5,910,142 A | 6/1999 | Tatar | ........................... | 606/61 |
| 5,938,663 A | * 8/1999 | Petreto | ........................ | 606/61 |
| 5,964,760 A | 10/1999 | Richelsoph | .................. | 606/61 |
| 5,984,922 A | 11/1999 | McKay | ........................ | 606/61 |
| 5,997,539 A | 12/1999 | Errico et al. | .................. | 606/61 |
| 6,010,503 A | 1/2000 | Richelsoph et al. | ......... | 606/61 |
| 6,030,388 A | 2/2000 | Yoshimi et al. | ............... | 606/61 |
| 6,063,090 A | 5/2000 | Schlaäpfer | .................... | 606/61 |
| 6,123,706 A | * 9/2000 | Lange | .......................... | 606/61 |
| 6,299,614 B1 | * 10/2001 | Kretschmer et al. | ......... | 606/60 |

FOREIGN PATENT DOCUMENTS

DE      86 09 102.6      5/1987

OTHER PUBLICATIONS

*EBI®Ωmega21™ Spinal Fixation System*, "Surgical Technique", by Mark K. Crawford, M.D., pp. 1–22; 12/99.

* cited by examiner

*Primary Examiner*—Pedro Philogene
(74) *Attorney, Agent, or Firm*—Woodard, Emhardt, Moriarty, McNett & Henry LLP

(57) ABSTRACT

A connection assembly between a spinal implant rod and a vertebral anchor. The assembly has a split ring, a clamp, a collet and optionally a nut. The split ring is located inside the clamp and the collet is inserted through each of the clamp's arms. In use, the spinal implant rod is placed inside the split ring and the shaft or shank of the vertebral anchor is placed inside the collet. Drawing the arms of the clamp together then tightens the connection assembly, which closes the collet around the vertebral anchor and closes the split ring around the implant rod. Threading a nut on one end of the collet or directly threading the collet into one of the arms of the clamp tightens the assembly.

20 Claims, 5 Drawing Sheets

MULTI-PLANAR ADJUSTABLE CONNECTOR

This invention relates to a laterally adjustable connection between a spinal rod and a vertebral anchor, and more particularly relates to a spinal implant connection that is dorsally adjustable.

BACKGROUND OF THE INVENTION

Spinal implant systems provide a rod for supporting the spine and for properly positioning components of the spine for various treatment purposes. Bolts, screws, and hooks are typically secured to the vertebrae for connection to the supporting rod. These vertebral anchors must frequently be positioned at various angles due the anatomical structure of the patient, the physiological problem being treated, and the preference of the physician. It is difficult to provide secure connections between the spinal support rod and these vertebral anchors at all the various angles and elevations that are required, especially where there are different distances between the rod and bolts and where these components are located at different heights on the patient.

One solution to this problem is shown in U.S. Pat. No. 5,938,663 to Petreto, the disclosure of which is specifically incorporated into this specification by reference. This patent describes a connection between a rod and a vertebral anchor, through which a surgeon may vary the angle between a spinal rod and the anchor to which the rod is attached. The connection is equipped with a ball joint that allows the surgeon to fix the desired angle between the anchor and the rod. This system, however, has no elevation adjustment capability after the bone anchor is installed because the clamp in that invention must be secured between a nut and an immovable shoulder on the bone anchor.

What is needed is a connection assembly between a spinal rod and a vertebral anchor that allows the surgeon to fix the desired elevation between a rod and the bone anchor as well as fix the desired angle between the anchor and rod. The following invention is one solution to that need.

SUMMARY OF THE INVENTION

In one aspect, this invention is a connection assembly between a spinal implant rod and a vertebral anchor. The connection assembly has a compressible ring to receive a portion of the spinal implant rod. The connection assembly also has a clamp to hold the compressible ring, and the clamp has two arms with a coaxial channel in each arm. The connection assembly also has a collet that is positioned inside the channels to hold the shaft of the vertebral anchor. A nut is then threadably engaged to the end of the collet extending from the clamp to tighten the connection assembly to the anchor and rod.

In another aspect, this invention is a connection assembly between a spinal implant rod and a vertebral anchor. The connection assembly has a compressible ring to receive a portion of the spinal implant rod. The connection assembly also has a clamp to hold the compressible ring, and the clamp has two arms with a coaxial channel in each arm. The connection assembly also has a collet that is positioned inside the channels to hold the shaft of the vertebral anchor. The collet is then threadably engaged to one of the arms of the clamp to tighten the connection assembly to the anchor and rod.

DETAILED DESCRIPTION OF THE PREFERRED EMBODIMENTS

Specific language is used in the following description to publicly disclose the invention and to convey its principles to others. No limits on the breadth of the patent rights based simply on using specific language are intended. Also included are any alterations and modifications to the description that should normally occur to one of average skill in this technology.

Figure 1:
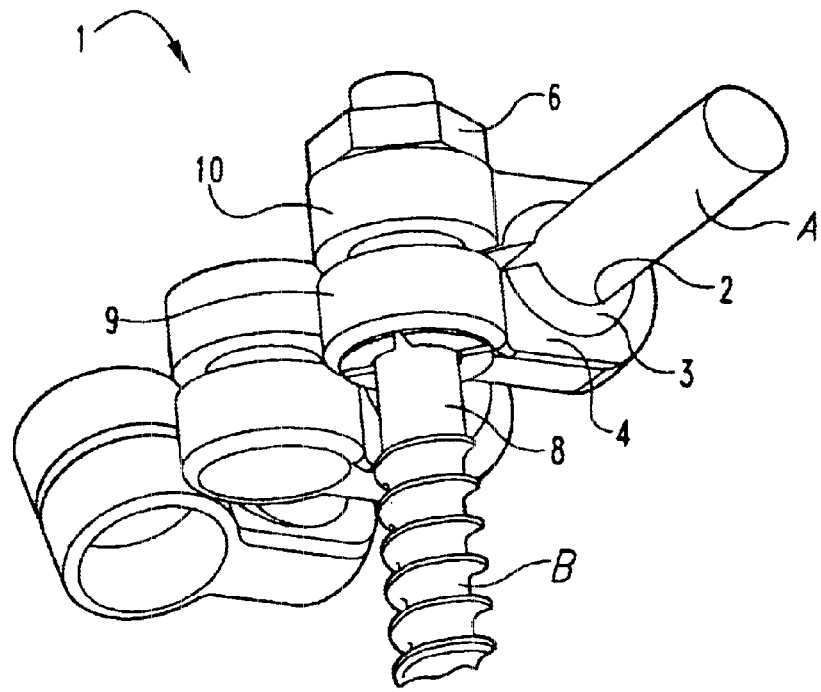
FIG. 1 is a perspective view of one embodiment of the invention.
Figure 2:
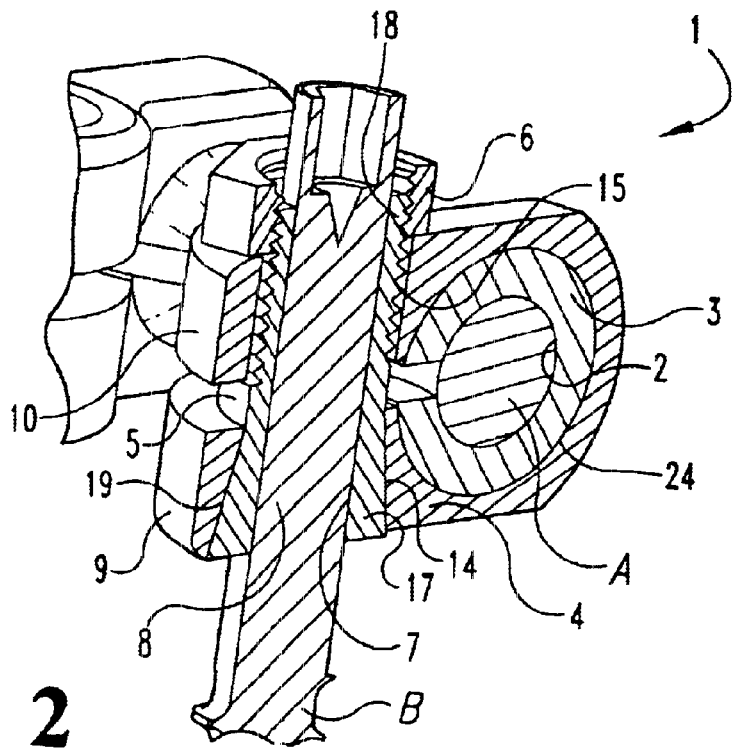
FIG. 2 is an elevational cross-sectional view of one embodiment of the invention.

A connection assembly 1 according to one embodiment of the invention is shown in FIGS. 1 and 2. Connection assembly 1 includes a compressible ring or split ring 3, a shackle or clamp 4, a collet 5, and a nut 6. Compressible ring 3 has an aperture 2 for receiving a rod "A" in a spinal implant system and collet 5 has a socket 7 for receiving the shank or post 8 of a vertebral anchor "B". As shown, socket is preferably open between the top and bottom of the connection assembly to allow post or shank 8 to extend through collet 5 so that collet 5 can be locked into place anywhere along the length of shank 8.

Figure 4:
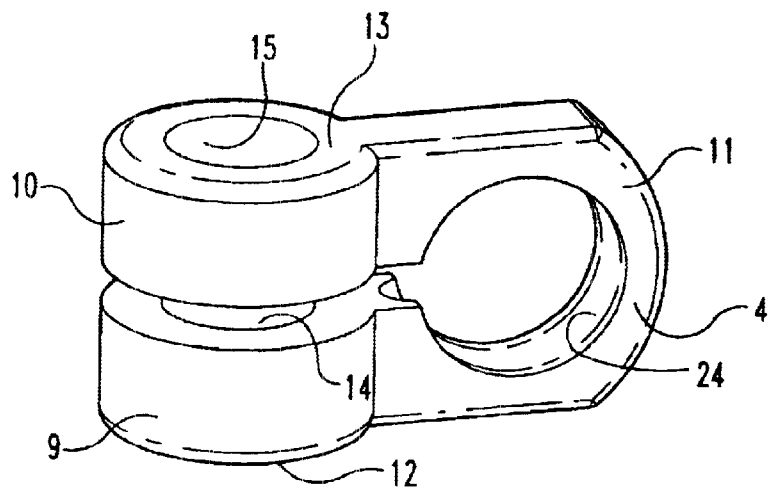
FIG. 4 is a perspective view of a clamp usable in one embodiment of the invention.

Referring to FIG. 4, shackle or clamp 4 has lower and upper branches (or arms) 9 and 10 and a head 11 that links these branches. The external faces 12 and 13 of branches 9 and 10 are preferably substantially flat; however, other surfaces are also contemplated. For example, the external face 12 of branch 9 may be countersunk for collet 5, or the external face 13 of branch 10 may be concave to accept a complementary convex surface on nut 6. Be that as it may, branches 9 and 10 have coaxially aligned channels 14 and 15 of appropriate diameter and contour to accept collet 5 inside clamp 4.

Figure 5:
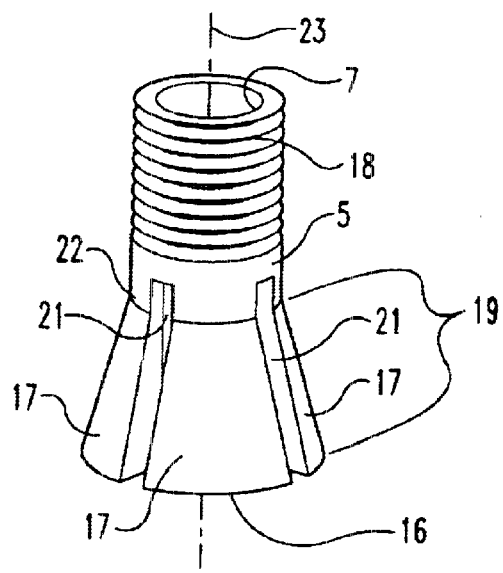
FIG. 5 is a perspective view of a collet usable in one embodiment of the invention.

Referring to FIG. 5, collet 5 is generally a cylindrical member having a first end 16 with multiple fingers 17, a threaded second end 18, and a tapered portion 19 between ends 16 and 18. Threaded second end 18 generally has a constant diameter that is readily accepted into channels 14 and 15 of clamp 4. The tapered portion 19 is flared in a fashion that widens over the length of collet 5, that is, widening as one moves from a position 22 on the interior surface of collet 5 and toward end 16. And though collet 5 is shown with a straight taper, it is also contemplated that the taper could be convex as well as concave over tapered portion 19. Regardless of the shape, channel 14 in clamp 4 (FIG. 2) contains a generally complementary profile to mate against whatever profile tapered portion 19 may have. That is, complementary in a manner that when collet 5 is forced into channel 14 beyond a position of mere contact against clamp 4, channel 14 will deflect fingers 17 inward toward the axis 23 of socket 7. Fingers 17 can be formed in most any fashion on collet 5. Preferably, however, they are integral and are formed in tapered portion 19 by placing a plurality of slots 21 that open between socket 7 and the exterior surface of collet 5 in the sides of collet 5.

Figure 7:
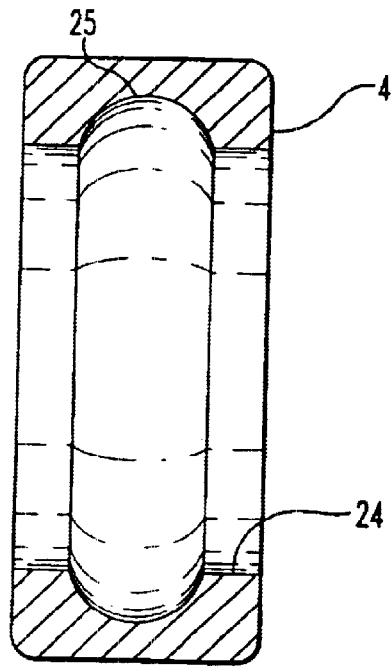
FIG. 7 is an end cross-sectional view of a clamp usable in one embodiment of the invention.
Figure 8:
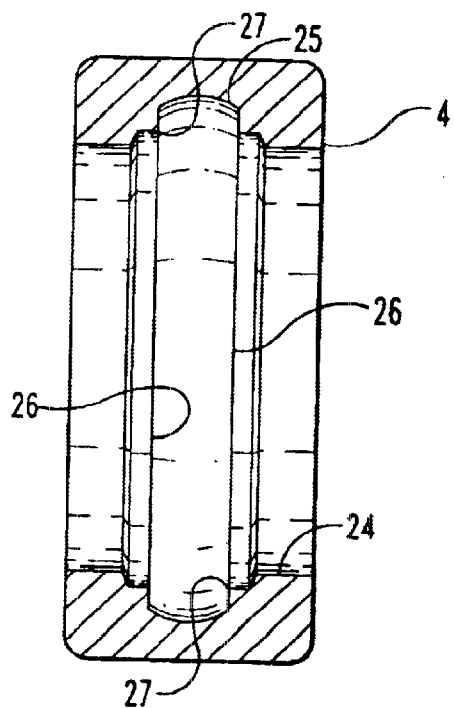
FIG. 8 is an end cross-sectional view of a clamp usable in one alternative embodiment of the invention.

Clamp 4 defines an interior cavity 24, which is preferably open on both sides of the clamp. Interior cavity 24 has a generally arched sidewall 25 (FIG. 7) that provides a concave surface to accept the generally sperical or convex exterior of compressible ring 3. Alternatively, interior cavity 24 could also include coaxial shoulders or arches 26 inside cavity 24. (FIG. 8) These shoulders 24 provide an edge 27 to grip compressible ring 3 when clamp 4 is later tightened.

Figure 3:
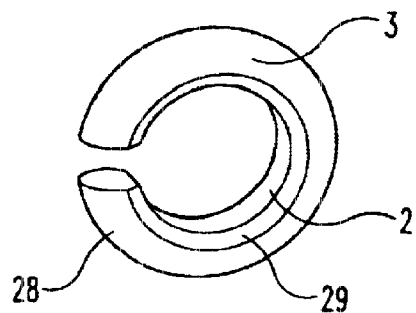
FIG. 3 is a perspective view of a compressible ring usable in one embodiment of the invention.

Referring to FIG. 3, compressible ring 3 has a preferably straight-through aperture 2 that is sized to receive spinal implant rod "A". The external face 28 of compressible ring 3 has a preferably generally spherical profile that is complementary to the interior profile of interior cavity 24 in clamp 4. As shown, ring 3 has a slot 30 that opens between the exterior 28 and aperture 2. Optionally, ring 3 may also have a groove 31 (FIG. 9) to further increase the ease with which the user may compress split ring 3. Moreover, ring 3 may also include a chamfer 29 around one or both sides of aperture 2 to assist the user in inserting the spinal implant rod "A" into connection assembly 1.

Referring back to FIGS. 1 and 2, screwing nut 6 onto the threaded second end 18 of collet 5 clamps the upper branch 10 and the lower branch 11 of clamp 4 together. This action, in turn, compresses split ring 3 that resides inside cavity 24 around spinal implant rod "A" and deflects fingers 17 of collet 3 around vertebral anchor "B". Compressing split ring 3 tightens assembly 1 to implant rod "A" and deflecting fingers 17 tightens assembly 1 to vertebral anchor "B". Optionally, the user may enhance this connection by roughening the surface of vertebral anchor "B", roughening the surface of implant rod "A", roughening the external face 28 of ring 3, or roughening the surface of interior cavity 24 of clamp 4.

Figure 6:
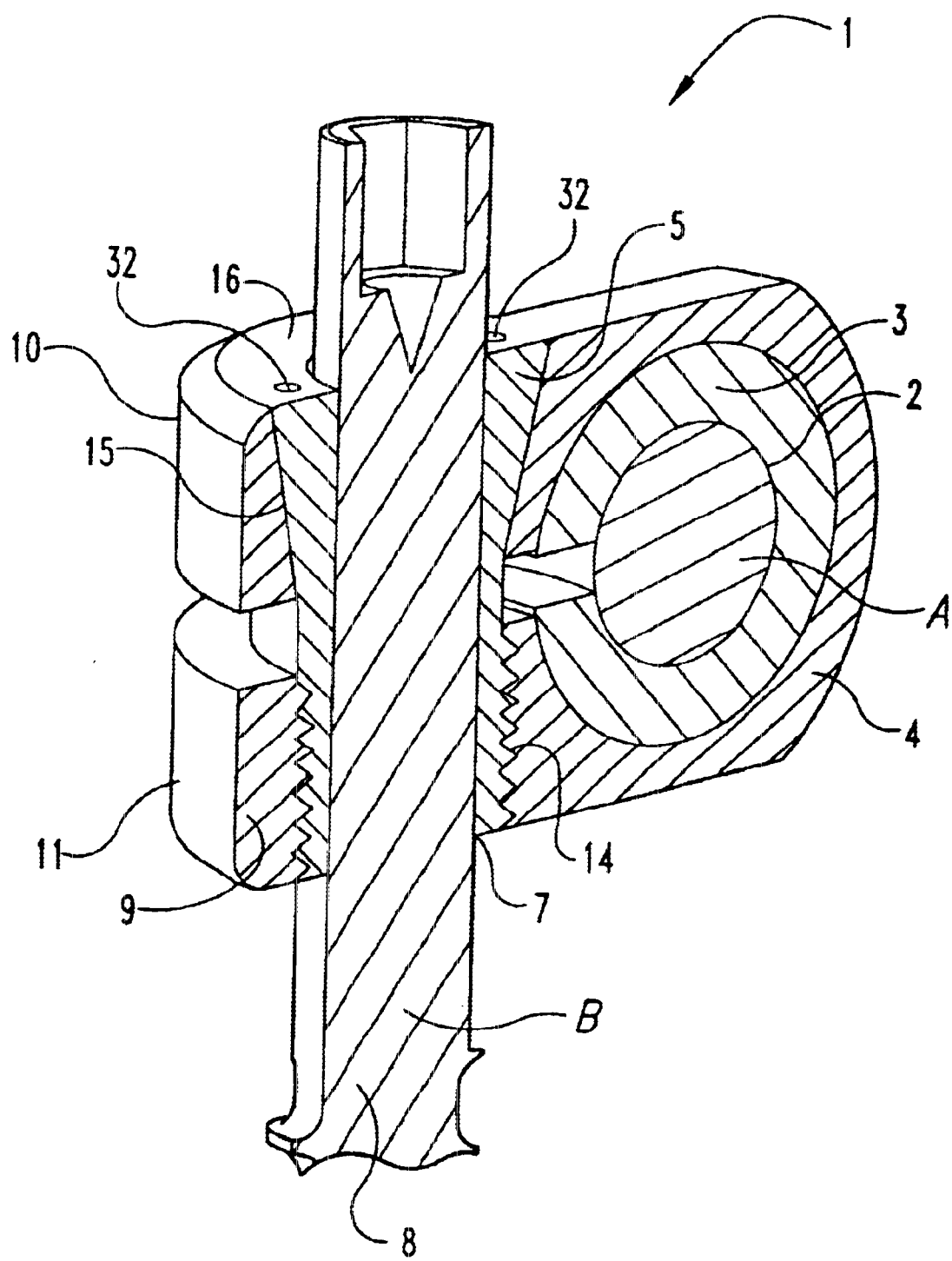
FIG. 6 is an elevational cross-sectional view of one alternative embodiment of the invention.

A variant of assembly 1 is shown in FIG. 6. In this embodiment, collet 3 is inverted and threads into the lower branch 9 of clamp 4. The inside of channel 15 in the upper branch 10 is then complementary tapered or profiled (as previously described in regard to channel 14) to accept the tapered portion 19 of collet 5. The collet is then rotated in this embodiment by a tool (not shown) that grips collet 5 by depressions or slots 32 in end 16. Turning collet 3 into the now threaded channel 14 clamps the upper branch 10 and the lower branch 11 of clamp 4 together. As with the previous embodiment, this action compresses split ring 3 around spinal implant rod "A" and deflects fingers 17 of collet 3 around vertebral anchor "B". Compressing split ring 3 tightens assembly 1 to implant rod "A" and deflecting fingers 17 tightens assembly 1 to vertebral anchor "B".

Figures 9, 10:
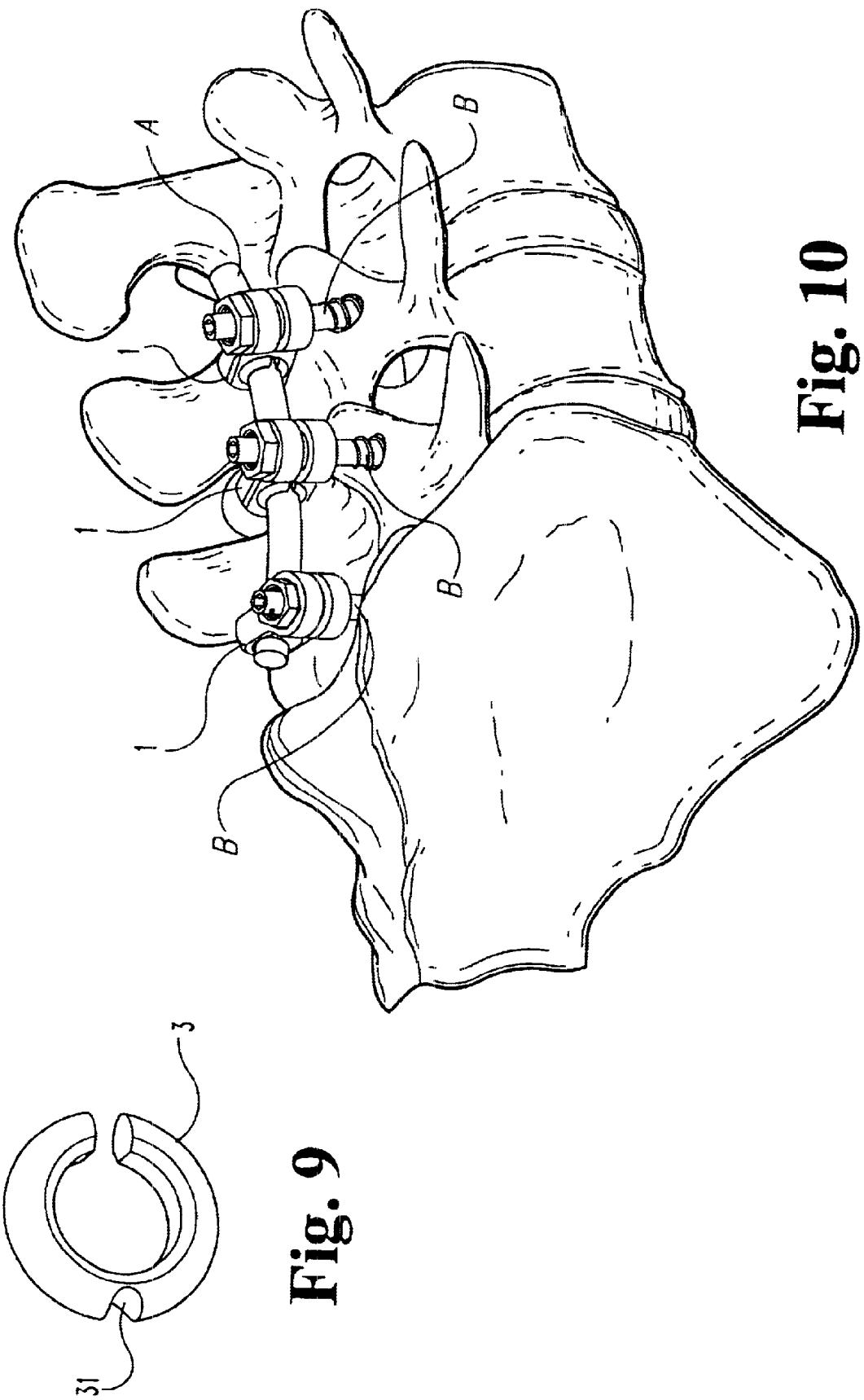
FIG. 9 is a perspective view of a compressible ring usable in one alternative embodiment of the invention.
FIG. 10 is a perspective view the invention installed in a portion of the human spine.

An installation of the connection assembly 1 is shown in FIG. 10. In general, the surgeon places the vertebral anchors into the pedicle of each vertebra. With the screws in place, a rod "A" is chosen having the desired rigidity, which is then bent to the necessary contour. The connection assemblies 1 are loaded onto the rod. Then the connectors 1 are sequentially lowered over the shanks of the vertebral anchors. Once placed at the desired elevation on each shank, the connection assemblies 1 are then tightened to secure the rod to the anchor by tightening nut 6 (FIGS. 1 and 2) or collet 5 (FIG. 6) depending on which embodiment of the invention is being used. Optionally, the surgeon may also place the connections on the anchors and then feed the rod through the connectors.

While the invention has been illustrated and described in detail, this is to be considered illustrative and not restrictive of the patent rights. The reader should understand that only the preferred embodiments have been presented and all changes and modifications that come within the spirit of the invention are included if the following claims or the legal equivalent of these claims describes them.

What is claimed is:

1. A connection assembly between a spinal implant rod and a vertebral anchor, the assembly comprising:
    (a) a compressible ring, said compressible ring defining an aperture to receive a portion of the spinal implant rod;
    (b) a clamp, said clamp defining a channel to hold said compressible ring, said clamp having first and second arms, said first arm having a first channel and said second arm having a second channel, one of said first channel or said second channel having a substantially straight internal taper; and
    (c) a collet, said collet positioned inside the first and second channels of said clamp, said collet defining a socket to hold the vertebral anchor, said collet having a first end and a second end and a portion with a substantially straight outside taper.

2. The connection assembly of claim 1 further including a nut, said nut threadably engaged to the first end of said collet.

3. The connection assembly of claim 1, wherein the second channel of said clamp has an internal taper in at least a portion of the second channel.

4. The connection assembly of claim 3, wherein the inside taper of the second arm of said clamp is complementary shaped to the outside taper of said collet.

5. The connection assembly of claim 1, wherein the compressible ring has at least a partially spherical exterior and the channel of said clamp has a substantially mating concave surface.

6. The connection assembly of claim 1, wherein the collet has three or more slots near the second end of said collet.

7. The connection assembly of claim 1, wherein the channel of said clamp has a sidewall and wherein at least a portion of the sidewall includes at least one edge to bear against the outside of said compressible ring.

8. The connection assembly of claim 1, wherein the compressible ring is split.

9. The connection assembly of claim 7, wherein the compressible ring has an exterior surface and wherein the compressible ring also includes a groove in the exterior surface.

10. The connection assembly of claim 1, wherein the taper of said collet widens near the second end of said collet.

11. A connection assembly between a spinal implant rod and a vertebral anchor, the assembly comprising:
    (a) a compressible ring, said compressible ring defining an aperture to receive a portion of the spinal implant rod;
    (b) a clamp, said clamp defining a channel to hold said compressible ring, said clamp having first and second arms, said first arm having a first channel and said second arm having a second channel;
    (c) a collet, said collet positioned inside the first and second channels of said clamp, said collet defining a socket to hold the vertebral anchor, said collet having a first end and a second end and an outside taper; said collet threadably engageable into the first channel of said first arm.

12. The connection assembly of claim 11, wherein the second channel of said clamp has an internal taper in at least a portion of the second channel.

13. The connection assembly of claim 12, wherein the inside taper of the second arm of said clamp is complementary shaped to the outside taper of said collet.

14. The connection assembly of claim 11, wherein the compressible ring has at least a partially spherical exterior and the channel of said clamp has a substantially mating concave surface.

15. The connection assembly of claim 11, wherein the collet has three or more slots near the second end of said collet.

16. The connection assembly of claim 11, wherein the channel of said clamp has a sidewall and wherein at least a portion of the sidewall includes at least one edge to bear against the outside of said compressible ring.

17. The connection assembly of claim 11, wherein the compressible ring is split.

18. The connection assembly of claim 17, wherein the compressible ring has an exterior surface and wherein the compressible ring also includes a groove in the exterior surface.

19. The connection assembly of claim 11, wherein the taper of said collet widens near the second end of said collet.

20. The connection assembly of claim 11, wherein said clamp is a shackle.

* * * * *